United States Patent [19]

Ives et al.

[11] Patent Number: 4,565,653

[45] Date of Patent: Jan. 21, 1986

[54] ACYLTRIPEPTIDE IMMUNOSTIMULANTS

[75] Inventors: Jeffrey L. Ives, Guilford; Frank C. Sciavolino, Niantic, both of Conn.

[73] Assignee: Pfizer Inc., New York, N.Y.

[21] Appl. No.: 595,169

[22] Filed: Mar. 30, 1984

[51] Int. Cl.$^4$ .......................................... C07C 103/52
[52] U.S. Cl. ............................................. 260/112.5 R
[58] Field of Search .................................. 260/112.5 R

[56] References Cited

U.S. PATENT DOCUMENTS 4,322,341  3/1982  Kitaura et al. ............... 260/112.5 R
4,493,794  1/1985  Kitaura et al. ............... 260/112.5 R

OTHER PUBLICATIONS

Kitaura et al., J. Med. Chem., 25, 335–337 (1982).

Primary Examiner—Delbert R. Phillips
Assistant Examiner—F. T. Moezie
Attorney, Agent, or Firm—Charles J. Knuth; Albert E. Frost; Peter C. Richardson

[57] ABSTRACT

Acyltripeptides having the formula below, pharmaceutically acceptable salts thereof and intermediates therefor; processes for their preparation and use as immunostimulant and antibacterial agents.

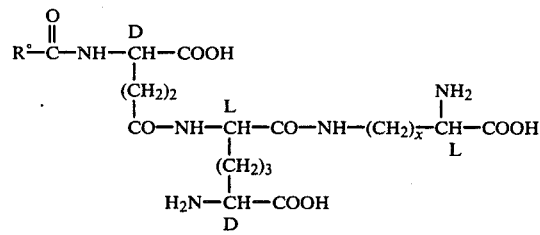

wherein R° is $C_{1-6}$alkyl; x is an integer and is 1 to 4.

9 Claims, No Drawings

ACYLTRIPEPTIDE IMMUNOSTIMULANTS

BACKGROUND OF THE INVENTION

1. Field of the Invention

This invention relates to novel acyltripeptides useful as immunostimulant and antibacterial agents; to pharmaceutically acceptable salts thereof; to intermediates therefor and to processes for their preparation.

2. Description of the Prior Art

The relatively new field of immunopharmacology, and particularly that segment thereof which deals with immunomodulation, continues to develop at a rapid pace. A variety of naturally occurring compounds has been investigated, including the tetrapeptide tuftsin, known chemically as $N^2$-[1-($N^2$-L-threonyl-L-lysyl)-L-prolyl]-L-arginine. Much attention has been directed to synthetic peptidoglycan derivatives, especially those known as muramyl dipeptides. For summaries of the wide range of compounds investigated as immunomodulators, and especially as immunostimulants, attention is directed to Dukar et al., Annu. Rep. Med. Chem., 14, 146–167 (1979), Lederer, J. Med. Chem., 23, 819–825 (1980) and to J. Kralovec, *Drugs of the Future*, 8, 615–638 (1983).

Immunostimulant peptides have been described in a number of patent specifications:

L-Alanyl-alpha-glutaric acid N-acyl dipeptides in German No. 3,024,355, published Jan. 15, 1981;

tetra- and penta-peptides containing D-alanyl-L-glutamyl moieties or L-alanyl-D-glutamyl moieties in British No. 2,053,231, published Feb. 4, 1981 and German No. 3,024,281, published Jan. 8, 1981, respectively; and N-acyl-L-alanyl-alpha-D-glutamyl tripeptide derivatives in which the C-terminal amino acid is lysine or diaminopimelic acid in German No. 3,024,369, published Jan. 15, 1981; and lactyl tetrapeptides composed of N-lactylalanyl, glutamyl, diaminopimelyl and carboxymethylamino components in EP No.-11283, published May 28, 1980.

Further immunostimulant polypeptides having the formula (A)

$$R^1-(HNCHCO)_n-HN-CH-R^3 \quad (A)$$
$$\underset{R^2}{|} \quad \underset{(CH_2)_m}{|}$$
$$CO-NH-CH-R^4$$
$$\underset{(CH_2)_3}{|}$$
$$R^6-HN-CH-R^5$$

wherein $R^1$ is hydrogen or acyl; $R^2$ is inter alia hydrogen, lower alkyl, hydroxymethyl, benzyl; $R^3$ and $R^4$ are each hydrogen, carboxy, —CONR$^7$R$^8$ wherein R$^7$ is hydrogen, lower alkyl optionally substituted with hydroxy; and R$^8$ is mono- or dicarboxy lower alkyl; R$^5$ is hydrogen or carboxy with the proviso that when one of R$^4$ and R$^5$ is hydrogen, the other is carboxy or —CONR$^7$R$^8$; R$^6$ is hydrogen; m is 1 to 3 and n is 0 to 2, and derivatives thereof in which the carboxy and amino groups are protected are disclosed in U.S. Pat. Nos. 4,311,640 and 4,322,341; EP applications Nos. 25,482; 50,856; 51,812; 53,388; 55,846 and 57,419.

None of the polypeptides disclosed in the art has a basic amino acid at the position occupied by variable R$^4$ in the above formula.

Kitaura et al., J. Med. Chem, 25, 335–337 (1982) report $N^2$—(gamma-D-glutamyl)-meso-2(L),2'(D)-diamino-pimelic acid as the minimal structure capable of eliciting a biological response characteristic of the compound of formula (A) wherein n is 1; $R^1$ is CH$_3$CH(OH)—CO—; $R^2$ is CH$_3$; each of R$^3$ and R$^5$ is —COOH; R$^4$ is —CONHCH$_2$COOH; and R$^6$ is H. Said compound of formula (A) is known as FK-156.

SUMMARY OF THE INVENTION

Novel acyltripeptides of formula (I)

$$\overset{O}{\underset{\|}{R^\circ-C}}-NH-\overset{D}{\underset{|}{CH}}-COOH \quad (I)$$
$$\underset{(CH_2)_2}{|}$$
$$CO-NH-\overset{L}{\underset{|}{CH}}-CO-NH-(CH_2)_{\overline{x}}\overset{NH_2}{\underset{L}{\overset{|}{CH}}}-COOH$$
$$\underset{(CH_2)_3}{|}$$
$$H_2N-\overset{|}{\underset{D}{CH}}-COOH$$

and pharmaceutically acceptable salts thereof are efficient immunostimulants or immunomodulators, and antibacterial agents. In the above formula:

R° is alkyl having from 1 to 6 carbon atoms and x is an integer from 1 to 4.

Also included in this invention are certain compounds useful as intermediates for production of compounds of formula (I). The intermediates have formulae (II) and (III).

$$\overset{O}{\underset{\|}{R^\circ-C}}-NH-\overset{D}{\underset{|}{CH}}-COOY^1 \quad (II)$$
$$\underset{(CH_2)_2}{|}$$
$$O=C-O-Y^2$$

and $$\overset{O}{\underset{\|}{R^\circ-C}}-NH-\overset{D}{\underset{|}{CH}}-COOY^1 \quad (III)$$
$$\underset{(CH_2)_2}{|}$$
$$CO-NH-\overset{L}{\underset{|}{CH}}-CO-Y^3$$
$$\underset{(CH_2)_3}{|}$$
$$HN-\overset{|}{CH}-CO-Y^4$$
$$\underset{Y^5}{|}$$
$$D$$

wherein
R° is C$_{1-6}$ alkyl;
each of and Y$^1$, Y$^2$ and Y$^4$ is a carboxy protecting group;
Y$^3$ is a carboxy protecting group or .

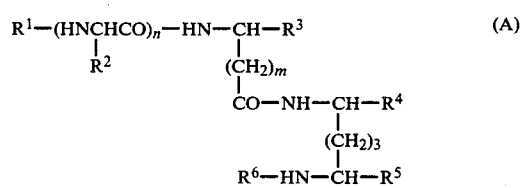

wherein x is an integer from 1 to 4; and $Y^5$ is an amino protecting group.

The configuration of the amino acid moieties which make up the formula I compounds is significant as regards the pharmacological activity of said compounds. The most potent activity is observed in formula I compounds having the stereochemistry indicated in said formula. The stereochemistry, relative to that of the natural amino acid, is designated as D- or L-. The stereochemistry of the

moiety can be either D- or L-, both epimers imparting potent activity to formula I compounds having the stereochemistry indicated at other sites.

The acyltripeptides of formula (I) are prepared by any of several methods known to those skilled in the art. The methodology involves the formation of peptide linkages between amino acids which, because of their amino and carboxy groups, and frequently the presence of other reactive groups, necessitate the protection of said groups and/or the activation of such groups, particularly the carboxy group, in order to achieve a certain reaction or to optimize such a reaction.

The overall reaction sequence involved is shown below.

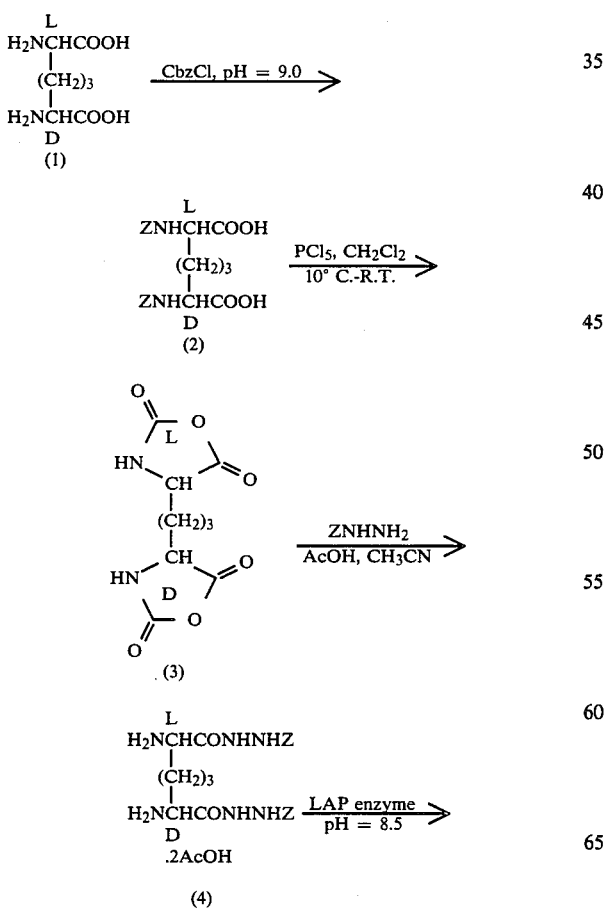

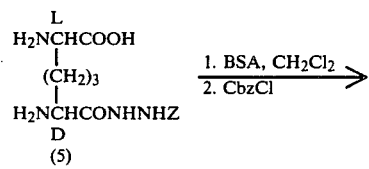

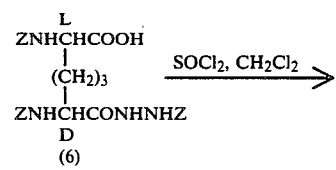

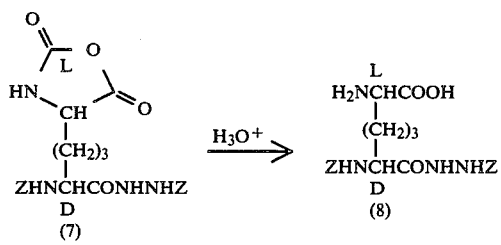

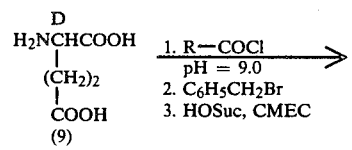

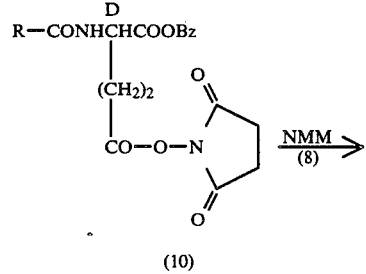

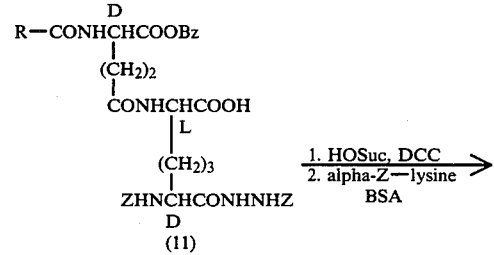

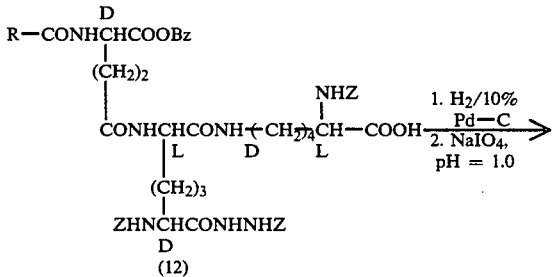

-continued

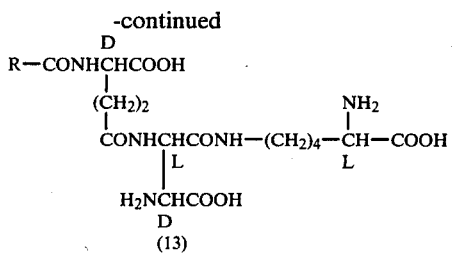

(13)

Z=Cbz=benzyloxycarbonyl
BSA=bis-trimethylsilylacetamide
CMEC=1-cyclohexyl-3-(2-morpholinoethyl)carbodiimide metho-p-toluene sulfonate
HOSuc=N-hydroxysuccinimide
NMM=N-methylmorpholine
R=($C_{1-6}$)alkyl
DCC=dicyclohexylcarbodiimide As is evident from the above reaction sequence, the amino acids which make up the tripeptide of formula (I) are prepared by joining the acylated glutamic acid to the diaminopimelic acid-lysine (or basic amino acid) dipeptide moiety. The dipeptide moiety is, in turn, prepared by joining diaminopimelic acid to lysine as per the above sequence. The order in which the individual amino acids are combined to produce the tripeptide is immaterial.

In the examples presented herein, certain protecting and activating groups are specifically illustrated. However, one skilled in the art will recognize that other protecting or activating groups could have been used. The choice of a particular protecting group is dependent to a great extent upon the availability of the necessary reagent, its effect upon solubility of the "protected" compound, its ease of removal and the presence of other groups which might be effected by its use; i.e. its selectivity, or its removal.

For example, it will be necessary, or at least desirable, in many reactions to protect the amino groups and/or the carboxy groups. The synthetic route chosen for the tripeptide synthesis may require removal of one or the other or both of said protecting groups in order to permit further reaction at the regenerated amino or carboxy group; i.e., the protecting groups used are reversible and, in most instances, are removable independently of each other. Additionally, the choice of protecting group for a given amino group depends upon the role of said amino group in the overall reaction scheme. Amino protecting groups having varying levels of lability, i.e., ease of removal, will be used. The same is true as regards carboxy protecting groups. Such groups are known in the art and attention is directed to the reviews by Bodansky et al., "Peptide Synthesis", 2nd Ed., John Wiley & Sons, N.Y. (1976); Greene, "Protective Groups in Organic Synthesis", John Wiley & Sons, N.Y. (1981); McOmie, "Protective Groups in Organic Chemistry", Plenum Press, N.Y. (1973); and to Sheppard in "Comprehensive Organic Chemistry, The Synthesis and Reactions of Organic Compounds", Pergaman Press, N.Y. (1979), edited by E. Haslam, Part 23.6, pages 321-339.

Conventional amino and carboxy protecting groups are known to those skilled in the art. Representative amino protecting groups, but by no means limiting thereof, are the following: such as benzyloxycarbonyl; substituted or unsubstituted aralkyl such as benzyl, trityl, benzhydryl and 4-nitrobenzyl; benzylidene; arylthio such as phenylthio, nitrophenylthio and trichlorophenylthio; phosphoryl derivatives such as dimethylphosphoryl and O,O-dibenzylphosphoryl; trialkylsilyl derivatives such as trimethylsilyl; and others as are described in U.S. Pat. No. 4,322,341 and which are incorporated herein by reference. The preferred amino protecting group is benzyloxycarbonyl. Procedures for substituting said group on a given amino group are well known. In general they comprise acylating the appropriate amino compound with benzyloxycarbonyl chloride (benzylchloroformate) in a reaction-inert solvent, e.g., water, methylene chloride, tetrahydrofuran, in the presence of a base (acid acceptor) e.g. sodium or potassium hydroxide when water is solvent; and, when an organic solvent is used, in the presence of a tertiary amine such as $C_{1-4}$ trialkylamines and pyridine. When an aqueous solvent system is used the pH of the reaction is held at about pH 8-10, and preferably at pH 9. Alternatively, when the reactant; i.e., the compound, an amino group of which is to be protected, contains basic groups, it can serve as acid acceptor.

The R—CO—acyl group is introduced into the glutamic acid reactant (compound 9 in the above sequence) by standard acylation procedures as by reacting said glutamic acid with the appropriate acid chloride or bromide in a reaction inert solvent. Favored conditions are aqueous systems, e.g., aqueous acetone, and a pH of 9.0, the pH being maintained at 8.5-9.0 by addition of a suitable base such as sodium or potassium hydroxide. Non-aqueous solvents can also be used. However, in such instances an organic base, preferably a tertiary amine such as triethylamine, N-methylmorpholine or pyridine is used as base.

The acylation can, of course, be accomplished by means of the appropriate acid anhydride (simple or mixed) according to standard procedures. When an anhydride is to be used for this acylation step, mixed anhydrides especially those derived from a low molecular weight carboxylic acid, and particularly the mixed carboxylic-carbonic anhydrides, are favored.

Representative carboxy protecting groups are various esters such as silyl esters, including trialkyl silyl esters, trihalosilyl esters and haloalkylsilyl esters; certain hydrocarbyl esters such as $C_{1-4}$ alkyl, especially t-butyl groups; benzyl and substituted benzyl esters, benzhydryl and trityl; phenacyl and phthalimidomethyl esters; certain substituted hydrocarbyl esters such as chloromethyl, 2,2,2-trichloroethyl, cyanomethyl; tetrahydropyranyl; methoxymethyl; methylthiomethyl; protected carbazoyl such as —CONH—NHR[5] wherein R[5] is an amino protecting group as disclosed above, especially benzyloxycarbonyl; and others as are described in U.S. Pat. No. 4,322,341 and which are incorporated herein by reference. The preferred carboxy protecting group is —CONH—NHR[5] wherein R[5] is benzyloxycarbonyl, said preferred group being referred to as benzyloxycarbonylcarbazide. A highly favored carboxy protecting group is the benzyl group.

The protected amino and carboxy groups are converted to the unprotected amino and carboxy groups by procedures known to those skilled in the art. The benzyloxycarbonyl group and the benzyl group, the preferred protecting groups for amino and carboxy (as part of the protected carbazoyl group) groups are removed by catalytic hydrogenation over palladium, especially palladium-on-carbon.

Selected removal of one benzyloxycarbonylcarbazide protecting group from meso-diaminopimelic acid dibenzyloxycarbonylcarbazide (product of Example 3 below) is conveniently accomplished by means of leucine aminopeptidase (LAP). The reaction is conducted in an aqueous solvent, especially in a mixture of water and a water miscible solvent (such as a $C_{1-4}$ alkanol, tetrahydrofuran, dioxane) at an alkaline pH, the pH range of 8-10 being favored; and a value of 8.5 being preferred.

Activation of carboxy groups as a means of expediting a given reaction is methodology known to those skilled in the art. Especially useful in the herein described reaction sequence are the use of anhydrides, particularly cyclic anhydrides; and activated esters, such as those derived from N-hydroxyphthalimide and N-hydroxysuccinimide, both of which are used in peptide syntheses.

In the herein described reaction sequence, intermediate compounds of formulae (2) and (6) contain alpha-substituted glycine moieties and are conveniently transformed to 2,5-oxazolidinedione derivatives (N-carboxy anhydrides) of formulae (3) and (7), respectively. Said anhydrides facilitate the subsequent reactions to which the formulae (3) and (7) compounds are subjected. They are formed by reacting the amino acid precursors of formulae (2) and (6) with a reagent such as $PCl_5$ or $SOCl_2$.

The activated N-hydroxysuccinimide esters [e.g., formula (10)] expedite subsequent reactions at said activated ester group. As the skilled artisan will recognize other activating groups could be used. A group of particular interest is the N-hydroxyphthalimido group, which group is used in the same manner as is the N-hydroxysuccinimido group. In both instances, a dehydrative coupling agent is used to form the activated ester. Representative of such coupling agents are 1-cyclohexyl-3-(2-morpholinoethyl)carbodiimide meth-od-p-toluene sulfonate, dicyclohexyl carbodiimide, N,N'-carbonyldiimidazole, N-(3-dimethylamino-propyl)-N'-ethylcarbodiimide hydrochloride, ethoxyacetylene, diphenylketene and N-ethyl-5-phenylisox-azoliene-3'-sulfonate. The reaction conditions for using such coupling agents are well described in the literature. In general they comprise the use of a reaction-inert solvent and temperatures ranging from ambient to 100° C. The above-mentioned carbodiimide reagents are favored since they permit use of ambient reaction temperature and afford satisfactory yields of the desired esters.

The products of this invention are useful as agents in mammals, including humans, for the clinical and therapeutic treatment of diseases caused by various pathogenic microorganisms, especially gram-negative bacteria. They are also useful as immunostimulants in mammals, including humans, having an increased risk of infection due to existing or clinically-induced immunosuppression.

The test procedure, which uses $C_3H/HeN$ male mice from the Charles River Breeding Laboratory, is presented below. The mice were acclimatized for 5 days before use and then treated either subcutaneously (SC) or orally (PO) with various dilutions (10, 1 and 0.1 mg/kg) of the test compound or placebo (pyrogen free saline) using a volume of 0.2 ml. The treatment regimen was dependent on the infectious organism utilized: $-24$ and 0 hours before challenge for *Klebsiella pneumoniae;* and $-6$, $-5$, $-4$ and $-1$ day before challenge for *Escherichia coli* or *Pseudomonas aeruginosa*. Challenge was administered intramuscularly (IM) in the hip in the case of *K. pneumoniae* or intraperitoneally (IP) in the case of *E. coli* and *P. aeruginosa*. A volume of 0.2 ml was used for the challenge. Mortality was recorded after 7 days in the case of *K. pneumoniae* and after 3 days in the case of the other two microorganism challenges.

Culture Preparation

*K. pneumoniae:* the culture was streaked for purity from frozen blood stock on brain heart infusion (BHI) agar. Three colonies were picked from the 18 hour plate culture and placed into 9 ml of BHI broth. The broth culture was grown for 2 hours at 37° C. on a rotary shaker after which 0.2 ml was streaked on the surface of several BHI agar slants. Following an 18 hour incubation at 37° C., the slants were washed with BHI broth, the culture density adjusted using a spectronic 20 and the appropriate dilution made to achieve an LD100 challenge level in mice (approx. 250 CFU/animal). (CFU=Colony forming units).

*E. coli* or *P. aeruginosa:* The culture was streaked for purity on the surface of a BHI agar plate from frozen blood stock. Following overnight incubation, several colonies were placed into 100 ml of Difco nutrient agar contained in a 250 ml Erlenmeyer flask. Following an 18 hour incubation at 30° C. on a New Brunswick rotary shaker, a 1:10 dilution was made into 90 ml of fresh nutrient broth. The culture was incubated at 30° C. (rotary shaker, 200 rpm) for 3 hours, the density adjusted to 78% using a spectronic 20, and the appropriate dilution made into BHI broth to achieve an LD90 by intraperitoneal injection into mice.

When used as antibacterial or immunostimulant agents in humans, the compounds of this invention are conveniently administered via the oral, subcutaneous, intramuscular, intravenous or intraperitoneal routes, generally in composition form. Such compositions include a pharmaceutical carrier selected on the basis of the chosen route of administration and standard pharmaceutical practice. For example, they can be administered in the form of tablets, pills, powders or granules containing such excipients as starch, milk sugar, certain types of clay, etc. They can be administered in capsules, in admixtures with the same or equivalent excipients. They can also be administered in the form of oral suspensions, solutions, emulsions, syrups and elixirs which may contain flavoring and coloring agents. For oral administration of the therapeutic agents of this invention, tablets or capsules containing from about 50 to about 500 mg are suitable for most applications.

The physician will determine the dosage which will be most suitable for an individual patient and it will vary with the age, weight and response of the particular patient and the route of administration. Generally, however, the initial dosage in adults may range from about 2-100 mg/kg per day in single or divided doses. The favored oral dosage range is from about 10 to about 300 mg/kg/day. The favored parenteral dose is from about 1.0 to about 100 mg/kg/day; the preferred range from about 0.1 to about 20 mg/kg/day.

This invention also provides pharmaceutical compositions, including unit dosage forms, valuable for the use of the herein described compounds for the utilities disclosed herein. The dosage form can be given in single or multiple doses, as previously noted, to achieve the daily dosage effective for a particular utility.

EXAMPLE 1

N,N'-Dibenzyloxycarbonyl-meso-diaminopimelic acid

To a solution of 209.4 g (1.1 mol) of meso-diaminopimelic acid in 2,200 ml of water, basified to pH 9.0 with 2N sodium hydroxide and cooled on an ice bath to 10° C., was added 450.5 g (2.64 mol) of benzylchloroformate over a 30 minute period. The pH was maintained throughout the addition at 9.0 with 2N sodium hydroxide. After 2.5 hours, the solution was extracted three times with one liter of ethyl acetate. The aqueous solution was acidified with 10% hydrochloric acid to pH 1.5 and extracted twice with one liter of ethyl acetate. The extracts were combined, dried over magnesium sulfate, filtered and concentrated, and the resulting oil was crystallized from 920 ml of chloroform at room temperature to yield 170 g (34%) of the title product: mp 129°–133° C.; IR (KBr) 2700, 1720, 1600 cm$^{-1}$; (D$_6$-DMSO) delta 7.1–7.4 (m, 10H), 5.2 (s, 4H), 4.0–4.2 (m, 2H), 1.2–1.6 (m, 6H); [alpha]$_D$=0.0 (C=1.2, MeOH).

EXAMPLE 2 meso-Diaminopimelic acid-di-N-carboxyanhydride

A suspension of 62.0 g (140 mmol) of N,N-dibenzyloxycarbonyl-meso-diaminopimelic acid in 1,240 ml dry methylene chloride was cooled under nitrogen atmosphere to 10° C. and treated in a single portion with 62.0 g (300 mmol) phosphorous pentachloride. The resulting yellow solution was stored one hour at 10° C. and allowed to warm to room temperature for 20 hours. The resulting suspension was filtered, the product washed successively with dry methylene chloride and dried under high vacuum to yield 29.9 g (91%) of the di-N-carboxyanhydride: mp 280° C.; IR (KBr) 3250, 1840, 1760 cm$^{-1}$; NMR (D$_6$-DMSO) delta 4.2–4.4 (m, 2H), 1.2–2.0 (m, 6H).

EXAMPLE 3 meso-Diaminopimelic acid-dibenzyloxycarbonylcarbazide diacetate

A stirred solution of 1.4 g (8.5 mmol) of benzyl carbazate in 4 ml of glacial acetic acid was cooled to 10° C., and the resulting slush was treated with 1.0 g (4.1 mmol) of meso-diaminopimelic acid-di-N-carboxyanhydride. The reaction was allowed to warm slowly to room temperature for two hours and the resulting oil triturated with ether to yield 2.37 g (95%) of the title product: mp 158°–161° C.; IR(Nujol) 2850, 1700 cm$^{-1}$; NMR (CD$_3$OD) delta 7.30 (s, 10H), 5.10 (s, 4H), 3.30 (m, 2H), 1.5–1.8 (m, 6H).

EXAMPLE 4 meso-Diaminopimelic acid-(D)-mono-benzyloxycarbonyl carbazide

A solution of 26.2 g (43 mmol) of meso-diaminopimelic acid-dibenzyloxycarbonylcarbazide diacetate in 325 ml of methanol and 750 ml of water was treated with 2N sodium hydroxide to pH 8.5. The resulting solution was treated with 2,200 units of leucine aminopeptidase (Sigma Hog Kidney, Type III suspension, Sigma Chemical Company, St. Louis, MO, U.S.A.) and stirred at room temperature for five days, maintaining the pH at 8.5 with 2N sodium hydroxide. The methanol was removed under vacuum, and the resulting aqueous solution was washed twice with 200 ml of ethyl acetate. The aqueous was applied to a HP-21 resin column. (HP 21 is a cross-linked styrene divinyl benzene copolymer in bead form having a macroreticular structure. It is available from V.G.F. Corporation, 420 Lexington Ave., New York, NY) The column was washed with two liters of water and then the product eluted with 50% methanol in water. The elutant was concentrated to give product which was triturated with ether, filtered and dried to give 14.1 g (95%) of the title product: mp 204°–210° C. (decomp.); IR (Nujol) 2200–3600, 1720, 1660, 1580 cm$^{-1}$; NMR (CD$_3$OD) delta 7.45 (s, 5H), 5.20 (s, 2H), 3.50 (m, 2H), 1.4–2.1 (m, 6H); [alpha]$^D$=−16.8 (C=1.0, AcOH).

EXAMPLE 5

N,N'-Dibenzyloxcarbonyl-meso-diaminopimelic acid mono-benzyloxycarbonylcarbazide A suspension of 11.8 g (35 mmol) of meso-diaminopimelic acid-(D)-mono-benzyloxycarbonylcarbazide in 270 ml of dry methylene chloride was treated with 56.8 ml (280 mmol) of bis-trimethylsilylacetamide and stirred at room temperature under nitrogen atmosphere for 18 hours. The reaction solution was cooled to −15° C. and treated over five minutes with 15.0 g (88 mmol) of benzylchloroformate. The reaction was stirred one hour at −15° C. and warmed to room temperature for 18 hours. The solution was acidified with dilute hydrochloric acid, stirred for one hour and then filtered to give 13.6 g (64%) of the title product: mp 141°–145° C.; IR (KBr) 3300, 1740, 1715, 1695, 1660 cm$^{-1}$; NMR (CD$_3$OD) delta 7.30 (s, 15H), 5.10 (s, 6H), 4.10 (m, 2H), 1.40–2.00 (m, 6H); [alpha]$^D$=+18.2 (C=0.6, MeOH).

EXAMPLE 6

Benzyloxycarbonyl-meso-diaminopimelic acid-mono-benzyloxycarbonylcarbazide

To a neat solution of 130 ml of thionyl chloride was added 13.0 g (21 mmol) of the title compound of Example 5. The solution was stirred two hours at room temperature, concentrated and dried under high vacuum for one hour. The resulting product was dissolved in 130 ml of acetic acid, treated with 65 ml of 1N hydrochloric acid and stirred at room temperature for 18 hours. The reaction was concentrated, and the resulting slurry was dissolved in 100 ml of water and neutralized with a solution of saturated sodium bicarbonate. The suspension was stirred one hour, filtered, washed with water and dried to give 9.7 g (93%) of the title product: mp 201°–205° C. (decomp.); IR (KBr) 3300, 1715, 1690, 1600 cm$^{-1}$; NMR (D$_6$-DMSO) delta 7.2–7.4 (bs, 10H), 5.25 (s, 2H), 5.20 (s, 2H), 4.40 (m, 2H), 1.6–2.5 (m, 6H); [alpha]$^D$=+35.1 (C=0.4, MeOH).

EXAMPLE 7

N-Heptanoyl-D-glutamic acid

A solution of 75.0 g (510 mmol) of D-glutamic acid in one liter of aqueous acetone (50:50) was adjusted to pH 9.0 with 2N sodium hydroxide. The resulting solution was cooled to 10° C. and treated over 45 minutes with 114.2 g (770 mmol) of heptanoyl chloride, maintaining the pH at 9.0 with 2N sodium hydroxide. The reaction was allowed to warm to room temperature for three hours. The acetone was removed under vacuum, and the resulting aqueous solution was acidified with dilute hydrochloric acid and extracted three times with 700 ml portions of ethyl acetate. The extracts were combined, dried over magnesium sulfate, filtered and concentrated. The resulting oil was triturated with hexane to give 109.8 g (83%) of desired product: mp 92°–96° C.; IR (Nujol) 3300, 2700–3250, 1720, 1625 cm$^{-1}$; NMR (D$_6$-DMSO) delta 4.20 (m, 1H), 2.28 (t, 2H), 2.20 (t, 2H), 1.85–2.05 (m, 1H), 1.65–1.85 (m, 1H), 1.40–1.60 (m, 2H), 1.15–1.30 (m, 6H), 0.75 (t, 3H); [alpha]$_D$= +9.6 (C=1.0, MeOH).

EXAMPLE 8

N-Heptanoyl-D-glutamic acid-alpha-benzyl ester

A solution of 108.8 g (420 mmol) of N-heptanoyl-D-glutamic acid and 50.6 g (500 mmol) of triethylamine in 135 ml of dimethylformamide was treated with 85.7 g (500 mmol) of benzyl bromide and stirred under nitrogen atmosphere for 60 hours. The reaction was poured onto one liter of ethyl acetate and washed successively with two 500 ml portions each of dilute hydrochloric acid and water. The ethyl acetate was then washed with 500 ml of 1N sodium hydroxide. The basic aqueous layer was acidified with dilute acid and extracted with four 500 ml portions of ethyl acetate. The combined ethyl acetate extracts were treated with excess dicyclohexylamine and stirred 18 hours. The suspension was filtered, slurried in fresh ethyl acetate (400 ml) for two hours, refiltered and dried under vacuum to give 49.1 g of dicyclohexylamine salt. The resulting salt (14.0 g) was stirred in dilute hydrochloric acid, filtered and washed with ethyl acetate. The aqueous filtrate was extracted twice with ethyl acetate, and the organic layers were combined, dried over magnesium sulfate, filtered and concentrated. The resulting oil was triturated with hexane to give 7.9 g (86% from salt) of the title ester: mp 76°–79° C.; IR (Nujol) 3300, 2700–3100, 1730, 1700, 1645 cm$^{-1}$; NMR (CDCl$_3$) delta 7.35 (s, 5H), 5.20 (s, 2H), 4.70 (m, 1H), 1.85–2.50 (m, 6H), 1.55–1.70 (m, 2H), 1.10–1.40 (m, 6H), 0.75 (t, 3H); [alpha]$_D$=27.6 (C=0.6, MeOH).

EXAMPLE 9

N-Heptanoyl-D-glutamic acid-alpha-benzyl-gamma-(N-hydroxysuccinimide)diester

A solution of 7.68 g (22 mmol) of N-heptanoyl-D-glutamic acid-alpha-benzyl ester and 6.1 g (51 mmol) of N-hydroxysuccinimide in 220 ml of ethyl acetate was treated with 22.9 g (51 mmol) of 1-cyclohexyl-3-(2-morpholinoethyl)carbodiimide metho-p-toluene sulfonate. The solution was stirred two days at room temperature and then poured onto 150 ml of water. The layers were separated, and the ethyl acetate portion was washed once with water, once with brine, dried over magnesium sulfate, filtered and concentrated. Triturated with ether gave 8.0 g (82%) of the title diester: mp 85°–89° C.; IR (Nujol) 3350, 2800–3000, 1810, 1790, 1745, 1650 cm$^{-1}$; NMR (CDCl$_3$) delta 7.30 (s, 5H), 5.20 (s, 2H), 2.8 (bs, 4H), 2.0–2.7 (m, 6H), 1.50–1.70 (m, 2H), 1.10–1.4 (m, 6H), 0.80 (t, 3H).

EXAMPLE 10

N-Heptanoyl-gamma-D-glutamyl-(alpha-benzyl ester)-benzyloxycarbonyl-(D)-meso-diaminopimelic acid-(D)-benzyloxycarbonyl-carbazide A solution of 4.22 g (9 mmol) of the title compound of Example 6 and 0.9 g (9 mmol) of N-methylmorpholine in 200 ml of 20% aqueous tetrahydrofuran was treated with 4.0 g (9 mmol) of N-heptanoyl-D-glutamic acid-alpha-benzyl-gamma-(N-hydroxysuccinimide)diester (product of Example 9). The reaction was stirred for two days at room temperature, concentrated and treated with 60 ml of 1N hydrochloric acid and 200 ml of ethyl acetate. The organic layers were combined, washed once with 1N HCl, once with brine, dried over magnesium sulfate, filtered and concentrated. Crystallization from ethyl acetate gave 4.94 g (69%) of title product: mp 139°–141° C.; IR (Nujol) 3300–2550, 1680, 1640 cm$^{-1}$; NMR (D$_6$-DMSO) delta 7.30 (bs, 15H), 5.12 (s, 2H), 5.08 (s, 2H), 5.00 (s, 2H), 4.25 (m, 1H), 4.15 (m, 1H), 4.00 (m, 1H), 2.25 (t, 2H), 2.10 (t, 2H), 1.20–2.00 (m, 16H), 0.80 (t, 3H); [alpha]$_D$= +22.4 (C =0.3, MeOH).

EXAMPLE 11

N-Heptanoyl-gamma-D-glutamyl-(alpha-benzyl ester)-benzyloxycarbonyl-(D)-meso-diaminopimelic acid-(D)-(benzyloxycarbonylcarbazide)-L-(N-hydroxysuccinimide) ester A solution of 3.70 g (4.6 mmole) of the title compound of Example 10 and 0.64 g (5.52 mmol) of N-hydroxysuccinimide 150 ml of 50% aqueous dioxane was cooled to 10° C. and treated with a single portion of 1.35 g (5.06 mmol) of N,N'-dicyclohexylcarbodiimide. The solution was stirred two hours at 10° C., 18 hours at room temperature, cooled again and filtered. The filtrate was evaporated, redissolved in ethyl acetate, filtered and concentrated. The resulting solid from the filtrate was triturated with ether to give 3.50 g (85%) of the title ester: mp 107°–110° C.; IR (KBr) 3600, 3100, 3000, 2950, 1810, 1740, 1710, 1645 cm$^{-1}$; NMR (D$_6$-DMSO) delta 7.35 (bs, 15H), 5.12 (s, 2H), 5.10 (s, 2H), 5.00 (s, 2H), 4.50 (m, 1H), 4.30 (m, 1H), 4.10 (m, 1H), 3.40 (bs, 4H), 1.20–2.40 (m, 20H), 0.85 (t, 3H).

EXAMPLE 12

N-Heptanoyl-gamma-D-glutamyl-(alpha-benzyl ester)-benzyloxycarbonyl-(D)-meso-diaminopimelic acid-(D)-(benzyloxycarbonylcarbazide)-(L)-N$^e$-(alpha-benzyloxycarbonyl)-L-lysine A suspension of 0.75 g (2.7 mmol) of alpha-benzyloxycarbonyl-L-lysine in 30 ml of dry methylene chloride was treated with 2.2 g (10.7 mmol) of bistrimethylsilyl acetamide and stirred 18 hours at room temperature. This solution was added to a 5° C. stirred solution of the ester of Example 11 in 100 ml of methylene chloride and 50 ml of tetrahydrofuran. The resulting solution was stirred one hour at 5° C. and allowed to warm slowly to room temperature. The solution was concentrated, treated with 300 ml of 0.7M HCl solution and extracted three times with ethyl acetate. The combined ethyl acetate layers were washed successively with water and brine, dried over magnesium sulfate, filtered and evaporated. The residue was dissolved in a minimal amount of hot ethyl acetate, cooled and filtered to give 2.06 g (80%) of the title product: mp 154°–157° C.; IR (KBr) 3600–3100, 3000, 2900, 1740, 1690, 1640 cm$^{-1}$; NMR (D$_6$-DMSO) delta 7.30 (bs, 20H), 5.14 (s, 2H), 5.09 (s, 2H), 5.02 (s, 2H), 4.98 (s, 2H), 4.30 (m, 1H), 4.15 (m, 1H), 3.95 (m, 2H), 3.00 (m, 2H), 2.20 (t, 3H), 2.15 (t, 3H), 1.10–2.10 (m, 22H), 0.85 (t, 3H).

EXAMPLE 13

N-Heptanoyl-gamma-D-glutamyl-L-meso-diaminopimelic acid-$N^e$-L-lysine

A solution of 1.0 g (0.94 mmol) of the protected tripeptide product of Example 12 and 250 mg of 10% palladium-on-carbon catalyst in 100 ml of 20% aqueous acetic acid was hydrogenated at 50 psi (3.52 kg/cm$^2$) of hydrogen gas for 24 hours. The solution was degassed, filtered and the filtrate concentrated. The residue was dissolved in 80 ml of 0.1N sulfuric acid, cooled to 5° C. and treated with 0.44 g (2.06 mmol) of sodium metaperiodate. The brown solution was stirred one hour at 5° C., treated dropwise with a saturated sodium bisulfite solution until clear and applied to a HP-21 resin column. The column was washed with water, and the desired compound was then eluted with 50% aqueous methanol. Evaporation of the elutant gave 0.46 g (88%) of the title acyltripeptide: mp 220° C. (decomp.); IR (KBr) 3650–2700, 1710, 1650, 1600 cm$^{-1}$; NMR (D$_2$O) delta 4.38 (m, 1H), 4.22 (m, 1H), 4.10 (m, 2H), 3.25 (m, 2H), 2.45 (t, 2H), 2.35 (t, 2H), 1.2–2.25 (m, 22H), 0.85 (t, 3H). $[alpha]_D = -18.8$ (C=0.5, H$_2$O).

EXAMPLE 14

N-Heptanoyl-gamma-D-glutamyl-(alpha-benzyl ester)-benzyloxycarbonyl-(D)-meso-diaminomelic acid (D)-(benzyloxycarbazide)-(L)-$N^e$-($N^a$-acetyl)-L-lysine methyl ester A solution of 0.895 g (3.75 mmol) of $N^a$-acetyl L-lysine methyl ester hydrochloride, 2.0 g (2.50 mmol) of the protected dipeptide product of Example 10 and 0.38 g (3.75 mmol) of N-methylmorpholine in 200 ml of tetrahydrofuran was cooled to 0° C. and treated with 0.51 g (3.75 mmol) of 1-hydroxybenzotriazole. The resulting solution was stirred 10 minutes and treated with 2.12 g (5.0 mmol) of 1-cyclohexyl-3-(2-morpholinoethyl)carbodiimide metho-p-toluenesulphonate. The solution was warmed to room temperature and stirred for 72 hours. The reaction was then concentrated, the residue dissolved in 200 ml of ethyl acetate and the solution washed with 200 ml of 2.5% aqueous hydrochloric acid. The resulting suspension was filtered without separation of the organic and aqueous phases to give a white solid which, upon recrystallization from hot tetrahydrofuran and diethyl ether, gave 1.64 g (66%) g of the title product: mp 174°–176° C.; IR (KBr) 3600–3100, 3000, 2950, 1740, 1690, 1660, 1640 cm$^{-1}$; NMR (D$_6$-DMSO) delta 7.35 (bs, 15H), 5.13 (s, 2H), 5.09 (s, 2H), 5.00 (s, 2H), 4.30 (m, 1H), 4.18 (m, 2H), 4.00 (m, 1H), 3.60 (s, 3H), 3.05 (m, 2H), 2.22 (t, 2H), 2.15 (t, 2H), 1.10–2.10 (m, 22H), 1.85 (s, 3H), 0.85 (t, 3H).

EXAMPLE 15

N-Heptanoyl-gama-D-glutamyl-L-meso-diaminopimelic acid-$N^e$-($N^a$-acetyl-L-lysine methyl ester)

A solution of 1.0 g (1.01 mmol) of the protected tripeptide product of Example 14 and 250 mg of 10% palladium-on-carbon in 50 ml of 20% aqueous acetic acid was hydrogenated under 50 psi of hydrogen for 1 hour. The solution was degassed, filtered and concentrated. The residue was dissolved in 50 ml water and 1 ml of tetrahydrofuran and the pH was adjusted to 2.0 with sulfuric acid. The solution was cooled to 5° C. and treated with 475 mg (2.22 mmol) of sodium metaperiodate, stirred 1 hour and then clarified with the dropwise addition of a saturated solution of sodium bisulfite. The solution was applied to a column of HP-21 resin, washed with water, and the product eluted with one liter of 30% aqueous methanol. The solution was concentrated and the resulting solid triturated with ether to give 434 mg (70%) of the desired product: mp 140° C. (dec.); IR (KBr) 3600–3100, 2950, 2850, 1740, 1640, 1620; NMR (D$_2$O) delta 4.35 (m, 2H), 4.20 (m, 1H), 3.80 (m, 1H), 3.80 (s, 3H), 3.20 (m, 2H), 2.45 (t, 2H), 2.30 (t, 2H), 1.20–2.25 (m, 22H), 2.05 (s, 3H), 0.85 (t, 3H); $[alpha]_{1.5}{}^D = -22.2$ (C=0.5, H$_2$O).

EXAMPLE 16

N-Heptanoyl-gamma-D-glutamyl-(alpha-benzyl ester)-benzyloxycarbonyl-(D)-meso-diaminopimelic acid-(D)-benzyloxycarbonyl)-L-$N^e$-($N^a$-acetyl)-L-lysine A solution of 0.50 g (2.67 mmol) of $N^a$-acetyl-L-lysine and 2.45 g (12.0 mmol) of bis(trimethylsilyl)acetamide in 50 ml of dry methylene chloride was stirred at room temperature for 18 hours. It was then added via syringe to a −15° C. solution of the isobutyl mixed anhydride of the product of Example 10, prepared by the addition of 0.29 g (2.24 mmol) of isobutyl chloroformate to a −15° C. solution of 1.78 g (2.2 mmol) of the Example 11 product and 0.24 g (2.2 mmol) of N-methylmorpholine in 100 ml of anhydrous tetrahydrofuran. The resulting reaction mixture was stirred 1 hour at −15° C. and 3 hours at room temperature. The reaction was concentrated, dissolved in 200 ml of ethyl acetate and washed with 200 ml of 2.5% aqueous hydrochloric acid. The ethyl acetate layer was separated, and concentrated to give a white solid which was triturated with ether to give 1.37 g (63%) of product; mp 170°–175° C.; IR (KBr) 3600–2850, 1740, 1680, 1750, 1600 cm$^{-1}$; NMR (D$_6$-DMSO) delta 7.35 (bs, 15H), 5.12 (s, 2H), 5.08 (s, 2H), 5.02 (s, 2H), 4.30 (m, 1H), 4.15 (m, 2H), 4.0 (m, 1H), 3.05 (m, 2H), 2.25 (m, 2H), 2.15 (t, 2H), 1.90 (s, 3H), 1.15–1.85 (m, 22H), 0.85 (t, 3H).

EXAMPLE 17

N-Heptanoyl-gamma-D-glutamyl-L-meso-diaminopimelic acid-$N^e$-($N^a$-acetyl)-L-lysine A solution of 1.2 g (1.23 mmol) of the product of Example 16 in 50 ml of 20% aqueous acetic acid was treated with 330 mg of 10% palladium-on-carbon catalyst and hydrogenated at 50 psi (3.52 kg/cm$^2$) of hydrogen for 1 hour. The solution was degassed, filtered and concentrated. The resulting oil was dissolved in 50 ml of water, cooled to 5° C. and acidified with sulfuric acid to pH 1.5–2.0. The resulting solution was then treated with 0.58 g (2.7 mmol) of sodium metaperiodate, stirred for 1 hour, the treated with a saturated solution of sodium bisulfite until clear. It was then applied to an HP-21 resin column and the column washed with 250 ml of water. Elution with 250 ml of 50% aqueous methanol gave, upon concentration, 0.55 g (74%) of desired product: mp 220° C. (dec.); IR (KBr) 3600–2900, 2850, 1720, 1640, 1540 cm$^{-1}$; NMR (D$_2$O) delta 4.30 (bm, 3H), 3.80 (t, 1H), 3.25 (m, 2H), 2.45 (t, 2H), 2.35 (t, 2H), 1.2–2.3 (m, 22H), 2.05 (s, 3H), 0.85 (t, 3H); $[alpha]_D = -17.6$ (C=0.5, H$_2$O).

EXAMPLE 18

N-Heptanoyl-gamma-D-glutamyl-(alpha-benzyl ester)-L-meso-diaminopimelic acid [(D)-benzyloxycarbonyl-(D)-benzyloxycarbonylcarbazide]-N$^d$-alpha-benzyloxycarbonyl-L-ornithine A suspension of 0.59 g (2.2 mmol) of alpha-benzyloxycarbonyl-L-ornithine in 80 ml of dry methylene chloride was treated with 1.81 g (8.9 mmol) of bis(trimethylsilyl)acetamide and stirred for 3 hours at room temperature. The resulting solution was added to a solution of the product of Example 11 ester in 70 ml of dry tetrahydrofuran and stirred at room temperature for 3 days. The resulting solution was concentrated and the residual oil treated with 500 ml of 0.7N aqueous hydrochloric acid and 350 ml of ethyl acetate. The two phase solution was stirred for 1.5 hours, separated and the organic layer concentrated and triturated with ether to give 1.95 g (84%) of the title product: mp 167°–171° C.; IR (KBr) 3600–3100, 2950, 1740, 1695, 1640; NMR (D$_6$-DMSO) delta 7.40 (m, 20H), 5.12 (s, 2H), 5.10 (s, 2H), 5.05 (s, 2H), 5.00 (s, 2H), 4.30 (m, 1H), 4.18 (m, 1H), 4.00 (m, 2H), 3.10 (m, 2H), 2.25 (t, 2H), 2.15 (t, 2H), 1.05–2.10 (m, 20H), 0.85 (t, 3H).

EXAMPLE 19

N-Heptanoyl-gamma-D-glutamyl-L-meso-diaminopimelic acid-N$^d$-L-ornithine

A solution of 1.40 g (1.33 mmol) of the product of Example 18 and 400 mg of 10% palladium-on-carbon in 150 ml of 20% aqueous acetic acid was hydrogenated at 45 psi (3.16 kg/cm$^2$) of hydrogen for 45 minutes. The solution was degassed, filtered and concentrated and resulting oil dissolved in 50 ml of water and acidified to pH=2.0 with concentrated sulfuric acid. The resulting solution was cooled to 5° C. and treated in one portion with 0.57 g (2.66 mmol) of sodium metaperiodate. The resulting brown solution was stirred for 1.5 hours, treated with a saturated solution of sodium bisulfite until clear, then applied to a column of HP-21 resin. The column was washed with 750 ml of water and the desired product was eluted with 400 ml of 50% aqueous methanol. The fractions containing the product were concentrated to give 0.52 g (71%) of the desired product: mp 230° C. (dec.); IR (KBr) 3600–3100, 2950, 1640, 1590; NMR (D$_6$-DMSO) delta 4.30 (m, 2H), 3.95 (m, 2H), 3.15 (m, 2H), 2.30 (t, 2H), 2.22 (t, 2H), 1.2–2.20 (m, 20H), 0.95 (t, 3H).

We claim:

1. A compound having formula (I)

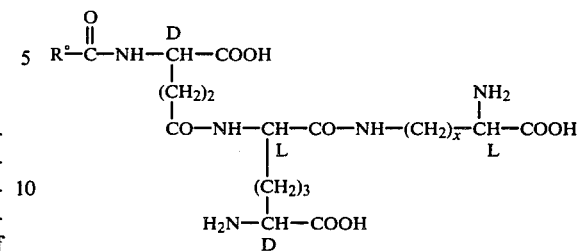

wherein R° is alkyl having from one to six carbon atoms, and x is an integer from 1 to 4.

2. A compound according to claim 1 wherein R° is alkyl having six carbon atoms and is n-hexyl.

3. The compound according to claim 2 wherein x is 4.

4. The compound according to claim 2 wherein x is 3.

5. A compound having the formula III

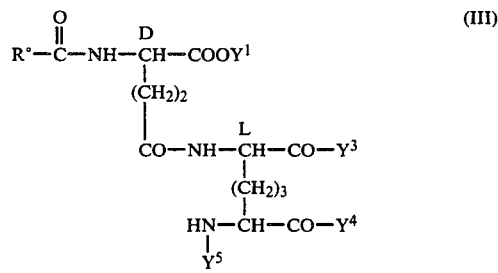

wherein R° is alkyl having from one to six carbon atoms; each of Y$^1$ and Y$^4$ is a carboxy protecting group; Y$^5$ is an amino protecting group; and Y$^3$ is

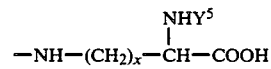

wherein x is an integer from 1 to 4.

6. A compound according to claim 5 wherein Y$^1$ is benzyl; Y$^4$ is benzyloxycarbonylcarbazide; Y$^3$ is

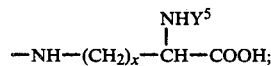

Y$^5$ is benzyloxycarbonyl; and x is an integer from 1 to 4.

7. A compound according to claim 6 wherein R° is n-hexyl.

8. The compound according to claim 7 wherein x is 4.

9. The compound according to claim 7 wherein x is 3.